US008158381B2

(12) United States Patent (10) Patent No.: US 8,158,381 B2
Wiederhold et al. (45) Date of Patent: Apr. 17, 2012

(54) METHODS FOR INTEGRATED TISSUE PROCESSING AND STAINING

(75) Inventors: J. Gary Wiederhold, Plainwell, MI (US); Nathan T. Brinn, Lake Zurich, IL (US)

(73) Assignee: Richard-Allan Scientific Company, Kalamazoo, MI (US)

(*) Notice: Subject to any disclaimer, the term of this patent is extended or adjusted under 35 U.S.C. 154(b) by 525 days.

(21) Appl. No.: 12/369,430

(22) Filed: Feb. 11, 2009

(65) Prior Publication Data

US 2009/0246824 A1 Oct. 1, 2009

Related U.S. Application Data

(60) Provisional application No. 61/070,996, filed on Mar. 27, 2008.

(51) Int. Cl.
*G01N 1/30* (2006.01)
(52) U.S. Cl. .................. 435/40.52; 435/40.5; 435/40.51
(58) Field of Classification Search ................. 435/40.5, 435/40.51, 40.52
See application file for complete search history.

(56) References Cited

U.S. PATENT DOCUMENTS

| | | | |
|---|---|---|---|
| 4,656,047 A | 4/1987 | Kok et al. | |
| 4,666,699 A | 5/1987 | Slifkin | |
| 4,839,194 A | 6/1989 | Malluche et al. | |
| 4,891,239 A | 1/1990 | Dudley et al. | |
| 4,911,915 A | 3/1990 | Fredenburgh | |
| 5,318,795 A * | 6/1994 | Stokes et al. | 427/4 |
| 5,482,676 A | 1/1996 | Camiener | |
| 5,508,175 A | 4/1996 | Slifkin | |
| 5,679,333 A | 10/1997 | Dunphy | |
| 5,830,352 A | 11/1998 | Holm | |
| 6,017,725 A | 1/2000 | Hoffmann et al. | |
| 6,042,874 A | 3/2000 | Visinoni et al. | |
| 6,207,408 B1 | 3/2001 | Essenfeld et al. | |
| 6,586,713 B2 | 7/2003 | Essenfeld et al. | |
| 6,902,928 B2 | 6/2005 | Izvoztchikov et al. | |
| 2005/0124028 A1 | 6/2005 | Windeyer et al. | |
| 2005/0255540 A1 | 11/2005 | Fredenburgh et al. | |

OTHER PUBLICATIONS

Zhao et al. (Chinese Journal of Zoology, 39:43-43, 2004) English Abstract only.
Pollard et al. (Journal of Histochemistry and Ctytochemistry, 1987, vol. 35, No. 11, pp. 1329-1338).
Werner et al. (The American Journal of Surgical Pathology, 2000, vol. 24, No. 7 pp. 1016-1019.

* cited by examiner

*Primary Examiner* — Taeyoon Kim
(74) *Attorney, Agent, or Firm* — Thompson Hine LLP

(57) ABSTRACT

Methods that combine processing and staining of tissue samples such that the processed tissue is stained and ready for histological evaluation prior to embedding and sectioning, and separate staining of the sectioned tissue is not required. The method may be used with chemical and/or mechanical/thermal tissue penetrant enhancers in an automated tissue processing system.

14 Claims, No Drawings

METHODS FOR INTEGRATED TISSUE PROCESSING AND STAINING

RELATED APPLICATION

This application claims priority to pending U.S. Provisional Patent Application Ser. No. 61/070,996 filed Mar. 27, 2008, which is incorporated herein in its entirety.

TECHNICAL FIELD

Methods that combine processing and staining tissue samples for histological evaluation.

DETAILED DESCRIPTION

The complete process for tissue histology preparations typically involves (i) tissue processing (fixation, dehydration, clearing and infiltration with embedding medium), (ii) sectioning and attaching sections to a microscope slide or other substrate, (iii) deparaffinization of tissue sections, and (iv) staining of tissue sections. To complete these steps, histology laboratories generally utilize a variety of instruments including automated processors of tissue samples, microtomes for preparing sections of processed samples, and automated stainers for preparing sections for microscopic examination or other analysis.

Much attention has been placed upon reducing the time needed for tissue processing. Little attention, however, has been focused elsewhere in the overall process after tissues are fixed and embedded, for example, sectioning and staining. Integration of tissue processing and staining steps would not only shorten the overall processing time by eliminating the need for post-sectioning staining, but would also lower costs by reducing technician hours and eliminating the need for a separate instrument for post-sectioning staining procedures.

U.S. Pat. Nos. 4,666,699 and 5,508,175 teach combination fixative-stain reagents for use in microscopic identification of enteric protozoa and other intestinal parasites. However, the reagents and procedures described are not generally acceptable for processing mammalian tissues. Neither patent describes the use of formalin fixative, the "gold standard" for processing of mammalian tissues and cells, and neither teaches the use of appropriate stains for distinguishing nuclear and cytoplasmic details, for example, hematoxylin and eosin routinely used for cytological and histological pathology procedures.

U.S. Pat. No. 5,482,676 teaches the use of a dye such as, for example, crystal violet, brilliant blue or bromocresol green, for coloring a specimen while in a fixative solution in order that the tissue is more readily visible for removal from the fixative solution and subsequent processing. The dye serves merely to color the outer surface of an unsectioned specimen and does not eliminate the later need for staining sections cut from the specimen for histologic evaluation.

Zhao et al. (Chinese Journal of Zoology, 39:42-43, 2004) teaches a manual processing method utilizing a glacial acetic acid/methanol fixative containing hematoxylin to fix and partially stain tissue specimens; hematoxylin reacts with nucleic acids and has little, if any, affinity for cytoplasmic proteins. As described, after tissues are fixed and embedded, sections are cut and dewaxed and then stained again, with eosin to distinguish the cytoplasm. The total processing time is at least 23 hours. Zhao et al. does not teach use of a standard formalin fixative and the disclosed procedure requires further staining of sections cut from the processed specimen with eosin or other cytoplasmic stains.

Without being held to a single theory, mammalian tissue samples have heretofore been required to be stained only after they have been sectioned, otherwise the stain was not able to adequately penetrate the thick tissue sample (typically 1 mm thick to 5 mm thick) to achieve uniform staining.

In the present method, in one embodiment, a tissue sample is stained during processing, that is, the method integrates tissue processing and staining. In one embodiment, the method stains and processes the tissue sample prior to infiltrating the tissue with embedding medium such that the tissue sample, after being embedded and sectioned, is ready for microscopic or other analysis, in the absence of further post-sectioning staining. In one embodiment the stain is hematoxylin. In one embodiment, the stain is eosin. In one embodiment, the stain is hematoxylin/eosin. Other stains may be used. In one embodiment, the stain is eosin-y. In one embodiment, the stain is phloxine-b. In one embodiment, the stain is eosin-y/phloxine-b.

In one embodiment, a kit contains reagents for tissue staining, tissue processing, or both tissue processing and tissue staining, and instructions for using the reagents in an integrated staining and processing method, such that the processed tissue is stained prior to embedding and additional staining is not required. In one embodiment, additional staining may optionally be performed.

In one embodiment, the method facilitates penetration of the stain into an unsectioned tissue sample. In one embodiment, the method facilitates penetration of the stain into an unsectioned tissue sample up to about 5 mm thick. In one embodiment, the method facilitates penetration of the stain into an unsectioned tissue sample between 1 mm thick and 5 mm thick. In one embodiment, the method facilitates penetration of the stain into an unsectioned tissue sample less than 1 mm thick. In any of these embodiments, the method results in more uniform staining of the tissue sample prior to sectioning. In one embodiment, the penetrant enhancer is provided by a chemical agent (e.g., dimethylsulfoxide). In one embodiment, the penetrant enhancer is provided by mechanical and/or thermal action (e.g., centrifugation, increased temperature). In one embodiment, the penetrant enhancer is provided by both a chemical agent and by mechanical/thermal action. In one embodiment, the use of an automated tissue processor, which applies heat and/or centrifugal pressure/agitation to the tissue sample, facilitates penetration of the stain into an unsectioned tissue sample prior to sectioning. In one embodiment, the method comprises using both tissue chemical penetrant enhancers and an automated tissue processor to facilitate stain penetration into an unsectioned tissue sample prior to sectioning. An example of an automated tissue processor includes STP 420 D instrument (Microm International/Thermo Fisher, Waldorf, Germany), described in U.S. Pat. No. 6,902,928.

Examples of tissue chemical penetrant enhancers that facilitate penetration of the stain into the tissue include, but are not limited to, polyethylene glycol (PEG), surfactants such as polyoxyethylenesorbitans, polyoxyethylene ethers (polyoxyethylenesorbitan monolaurate (Tween 20) and other Tween derivatives, polyoxyethylene 23 lauryl ether (Brij 35), Triton X-100, Brij 35, Nonidet P-40, detergent-like substances such as lysolecithins, saponins, non-ionic detergents such as TRITON® X-100, etc., aprotic solvents such as dimethyl sulfoxide (DMSO), ethers such as tetrahydrofuran, dioxane, etc.; esters such as ethyl acetate, butyl acetate, isopropyl acetate; hydrocarbons such as toluene, chlorinated solvents such as dichloromethane, dichloroethane, chlorobenzene, etc.; ketones such as acetone, nitriles such as acetonitrile, and/or other agents that increase cell membrane permeability. In one embodiment, more than one tissue chemical penetrant enhancer is used in the method. In one embodiment, the concentration of the tissue chemical penetrant enhancer ranges from about 1% v/v to about 10% v/v. In one embodiment, the concentration of the tissue chemical penetrant enhancer ranges from about 1% v/v to about 5% v/v. In one embodiment, the concentration of the tissue chemical penetrant enhancer ranges from about 5% v/v to about 10% v/v. In one embodiment, the concentration of the tissue chemical penetrant enhancer ranges from about 1% v/v to about 2% v/v. In one embodiment, the concentration of the tissue chemical penetrant enhancer ranges from about 2% v/v to about 5% v/v. In one embodiment, the concentration of the tissue chemical penetrant enhancer ranges from about 5% v/v to about 7% v/v. In one embodiment, the concentration of the tissue chemical penetrant enhancer ranges from about 7% v/v to about 10% v/v.

In one embodiment, a composition is provided that facilitates staining of a mammalian tissue sample prior to embedding and sectioning of the sample. The composition comprises a stain, such as hematoxylin, or hematoxylin and eosin-Y. In one embodiment, the composition comprises a stain, such as hematoxylin, or hematoxylin and eosin-Y, and at least one tissue chemical penetrant enhancer, such as a surfactant, an aprotic solvent, and/or PEG. In one embodiment, the concentration of hematoxylin ranges from about 2% v/v to about 4% v/v. In one embodiment, the concentration of eosin-Y ranges from about 3% v/v to about 5% v/v. In one embodiment, the concentration of hematoxylin is about 3.7% v/v. In one embodiment, the concentration of eosin-Y is about 4.5% v/v. In one embodiment, the concentration of the tissue chemical penetrant enhancer ranges from about 1% v/v to about 10% v/v. In one embodiment, the concentration of the tissue chemical penetrant enhancer is about 5% v/v.

The staining composition may be used in conjunction with an automated tissue processor, as described above.

Staining of the tissue sample may occur at any point in the processing of the tissue sample prior to infiltrating the tissue sample with embedding medium and sectioning. As only one non-limiting example, the tissue sample may be stained during the dehydration step of tissue processing. As another non-limiting example, the tissue sample may be stained before the dehydration step of tissue processing. As another non-limiting example, the tissue sample may be stained after the dehydration step of tissue processing.

In one embodiment, a method for dehydrating and staining of a fixed tissue sample prior to infiltrating with embedding medium is provided. In one embodiment, the tissue sample is between about 1 mm and 5 mm thick. In one embodiment, the tissue is mammalian tissue. In one embodiment, the tissue is not a liquid. In one embodiment, the method comprises, in sequential order: (a) exposing the fixed tissue sample to a hematoxylin stain; (b) exposing the tissue sample to an aqueous alcohol solution; (c) exposing the tissue sample to an eosin-Y stain; and (d) dehydrating the tissue sample, then infiltrating the sample with an embedding medium. In one embodiment, the method comprises, in sequential order: (a) exposing the fixed tissue sample to a stain reagent comprising hematoxylin, an oxidizer and a mordant; (b) exposing the tissue sample to an aqueous solution comprising about 85% v/v to about 95% v/v reagent grade alcohol at about pH 8.2 to about pH 8.5; (c) exposing the tissue sample to a stain reagent comprising eosin-Y in an acidic alcohol solution comprising about 80% v/v alcohol at about pH 4.5 to about pH 4.8; and (d) dehydrating the tissue sample, and infiltrating the sample with an embedding medium.

Tissue fixation can occur by various methods as known to a person of ordinary skill in the art. Tissue fixation may be performed manually or with an automated tissue processor, for example, STP 420 D instrument (Microm International/Thermo Fisher, Waldorf, Germany). In one embodiment, the tissue is fixed in a STP 420 D instrument using a fixative solution at about 55° C. to about 57° C. using centrifugal pressure/agitation at a medium setting of about 12 rpm. In one embodiment, the tissue is fixed for about 20 minutes to about 25 minutes for samples up to about 3 mm thick; about 25 minutes to about 30 minutes for samples between about 3 mm and about 4 mm in thick; and about 30 minutes to about 40 minutes for samples between about 4 mm and about 5 mm thick. In another embodiment, the tissue sample is fixed in fixative solution at about 21° C. to about 25° C. (e.g., room temperature) overnight without centrifugation.

Various fixative solutions may be used to fix the tissue sample. For example, any fixative appropriate for preservation of the particular tissue sample may be used. These include, but are not limited to, formaldehyde, glutaraldehyde, paraformaldehyde, formalin, methanol, ethanol, isopropanol, acetone acetic acid, and/or picric acid. In one embodiment, neutral-buffered formalin, which is the most commonly used fixative for mammalian tissues, is used. In one embodiment, neutral-buffered formalin at pH ranging from about pH 6.8 to about pH 7.2 in an aqueous alcohol solution, is used. The aqueous alcohol solution can be, for example, 95% ethanol, or a blend of 85% ethanol, 5% methanol, 5% isopropanol. In one embodiment, additives such as DMSO and/or PEG, such as PEG 400, is used. In one embodiment, the fixative solution comprises about 10% v/v formalin, about 82% v/v to about 85% v/v reagent grade alcohol, about 2% v/v to about 5% v/v DMSO, about 2% v/v deionized water, about 1% v/v PEG 400, and about 0.02% v/v sodium acetate buffer. In one embodiment, the dehydrant is ethanol. In one embodiment, the dehydrant is denatured ethanol. In one embodiment, the dehydrant is 100% ethanol. In one embodiment, the dehydrant is a mixture comprising at least about 90% ethanol, e.g., 90% ethanol, 5% methanol and 5% isopropanol.

Following fixation, the tissue sample is processed and stained according to the method. In one embodiment, the method, as described below, is performed using an automatic tissue processor, such as the STP 420 D instrument, using centrifugal pressure (in one embodiment, about 12 rpm, at the temperature and time settings indicated in each step. However, the method is not limited to the use of automated tissue processors for each step, or to any particular brand or model of tissue processor.

The fixed tissue sample is subjected to hematoxylin staining. In one embodiment, the tissue sample is exposed to a hematoxylin solution at a concentration of about 3.7% v/v for about 5.5 hours at about 55° C. using centrifugal pressure. In one embodiment, the hematoxylin solution is an aqueous solution containing hematoxylin (Richard-Allan Scientific Hematoxylin, Thermo Fisher Scientific, Kalamazoo Mich.), an oxidizer to convert hematoxylin to hematein, and a mordant, for creating a hematoxylin-dye lake. In one embodiment, the oxidizer is sodium iodate. In one embodiment, the oxidizer is periodic acid. In one embodiment, the mordant is aluminum ammonium sulfate. In one embodiment, the mordant is aluminum potassium sulfate. In one embodiment, the mordant is ferric ammonium sulfate. In one embodiment, the mordant is aluminum sodium sulfate. In one embodiment, the mordant is ferric ammonium sulfate. In one embodiment, a tissue chemical penetrant enhancer such as DMSO, PEG and/or surfactant may be included in the hematoxylin solution. In one embodiment, the hematoxylin solution is prepared by combining 210.9 g aluminum ammonium sulfate, 14.06 g hematoxylin, 2.09 g sodium iodate, 1000 ml DMSO, 950 ml ethylene glycol, 76 ml PEG 400, 5 ml Triton X-100, 1693 ml deionized (DI) water, and the pH is adjusted to between about pH 2.5 and about 2.8 using glacial acetic acid.

In one embodiment, the tissue sample is pre-treated with a bluing solution prior to staining with the hematoxylin solution. The bluing solution increases hematoxylin-dye-lake binding to the tissue sample. Without being held to a single theory, treatment with the bluing solution increases hematoxylin binding to the tissue sample by causing chelation of a molecule of hematein to the hematein-dye-lake complex. The bluing solution enhances the bluish hue of nuclear chromatin, providing optimal contrast with the pink eosin-y hue. In one embodiment, the bluing solution is an aqueous cationic solution buffered to maintain pH at about pH 8, for example, Richard-Allan Scientific Bluing Reagent (Thermo Fisher Scientific, Kalamazoo Mich.). In one embodiment, the tissue sample is exposed to Richard-Allan Scientific Bluing Reagent at room temperature (about 20° C. to about 22° C.) for about 10 minutes with centrifugal pressure.

In one embodiment, the tissue sample is stained and then dehydrated. In one embodiment, the tissue sample is dehydrated and then stained. In one embodiment, the tissue sample is stained during dehydration. In any of these embodiments, any of dehydration solutions termed I, II, and III may be used. Dehydration I solution is about 80% v/v reagent grade alcohol in deionized water. Dehydration II solution is about 85% v/v to about 95% v/v reagent grade alcohol in an aqueous buffer at about pH 8.2 to about pH 8.5. In one embodiment, dehydration II solution additionally contains reagents for bluing of cell nuclei in the tissue sample, such as Richard-Allan Scientific Bluing Reagent. In one embodiment, dehydration II solution additionally contains a tissue chemical penetrant enhancer such as DMSO, e.g., 7.5% v/v, and/or PEG, e.g., 1.0% v/v, for better penetration. In one embodiment, dehydration II solution contains about 85% v/v to about 87% v/v reagent grade ethanol in deionized water, ammonium hydroxide at about 0.5% to about 2.0% v/v and, optionally, DMSO at about 7.5% v/v, PEG 400 at about 1% v/v, sodium bicarbonate at about 2 g/L, and/or magnesium sulfate at about 10 g/L. In one embodiment, dehydration III solution contains about 95% v/v to about 98% v/v reagent grade alcohol in deionized water and, optionally, about 1.3% v/v DMSO, about 0.025% v/v TRITON X-100®, and/or about 0.2% w/v eosin-Y. In one embodiment, the tissue sample is rinsed in dehydration I solution for about 10 minutes at about 30° C. with centrifugal pressure, then rinsed in dehydration II solution for about 10 minutes at about 30° C. with centrifugal pressure, and then rinsed in dehydration III solution for about 25 minutes at about 25° C. with centrifugal pressure. In another embodiment, the tissue sample is rinsed and/or immersed in dehydration II solution for about 10 minutes at about 30° C. with centrifugal pressure.

In one embodiment, the hemotoxylin-stained tissue sample is further subjected to eosin staining. In one embodiment, the tissue sample is exposed to a eosin solution for about 75 minutes at about 20° C. to about 22° C. with centrifugal pressure. In one embodiment, the eosin solution contains about 80% v/v reagent grade alcohol and about 0.45% w/v eosin-Y, pH adjusted to between about pH 4.5 and about pH 4.8 with glacial acetic acid. Optionally, the eosin solution also contains about 18.4% v/v DMSO and/or about 0.045% v/v TRITON X-100®. In one embodiment, the eosin solution is prepared by combining 3021 ml reagent grade alcohol, 17.1 g eosin-Y, 700 ml DMSO, 50 ml deionized water, 10 ml TRITON X-100®, and about 500 ml glacial acetic acid to adjust the pH to pH 4.5 to pH 4.8.

The stained tissue sample is then rinsed. In one embodiment, the stained tissue sample is rinsed in dehydration I solution, as described above, for about 20 minutes at about 20° C. to about 22° C. with centrifugal pressure.

The stained and rinsed tissue sample is then subjected to a final dehydration. In one embodiment, the tissue sample is exposed to 100% reagent grade alcohol or equivalent, such as denatured ethanol containing 90% v/v ethyl alcohol, 5% v/v methyl alcohol, and 5% v/v isopropyl alcohol, for about 65 minutes at about 20° C. to about 22° C. with centrifugal pressure.

The stained, rinsed, and dehydrated tissue sample is then cleared. In one embodiment, clearing is by exposing the tissue sample to a clearing solution comprising 100% xylene at about 45° C. for about 25 minutes with centrifugal pressure.

The tissue sample is then infiltrated with an embedding medium. In one embodiment, the tissue sample is treated with paraffin, for example, Type I paraffin, at about 62° C. for about 45 minutes with centrifugal pressure. The infiltration step may be repeated.

At any point in the method prior to staining, the tissue sample may be placed in a holding solution. For example, the holding solution may be used to transport, and/or briefly store, a tissue sample from a collection site to a processing area. In one embodiment, tissue samples up to 5 mm at thickest point may be placed in a holding solution at 25° C. for up to six hours. In one embodiment, the holding solution is a buffered formalin/alcohol solution. In one embodiment, the holding solution contains about 9% v/v to about 11% v/v formalin in about 80% reagent grade alcohol buffered with sodium acetate to a pH of about pH 6.8 to about pH 7.2. In one embodiment, the holding solution contains non-ionic detergents such as Triton-X 100, Tween 20, or Nonidet P-40, etc., and/or aprotic solvents such as DMSO, or other reagents that increase cell membrane permeability. In one embodiment, the holding solution contains formalin at about 9% v/v to about 11% v/v buffered to between about pH 6.8 to about pH 7.2, about 80% v/v reagent alcohol, about 0.02% v/v sodium acetate buffer, about 0.1% v/v to about 1.0% v/v TRITON X-100®, and about 0.1% v/v to about 1.0% v/v DMSO.

The above method has successfully processed and stained various human tissues including liver, kidney, heart, lung, spleen, pancreas, tonsil, lymph node, placenta, skin, brain, uterus, colon, bone, breast, gall bladder, prostate, adipose tissue, appendix, skeletal muscle, bone marrow, ovary, thyroid, urinary, and bladder.

Other variations or embodiments will also be apparent to one of ordinary skill in the art from the above description. For example, the method may be used with stains other than hematoxylin and/or eosin. For example, the stained tissue sample may be further subjected to, e.g., special stains, immunohistochemistry, in situ hybridization, etc. Thus, the foregoing embodiments are not to be construed as limiting the scope of the following claims.

What is claimed is:
1. A method for integrated histological tissue staining and processing, the method comprising
    exposing a fixed tissue sample to at least one histological stain in the presence of at least one of a chemical tissue penetrant enhancer during or before a tissue processing dehydration step; and
    thereafter clearing the stained tissue to result in a processed and stained tissue sample ready for infiltrating with an embedding medium and sectioning in preparation for histological evaluation without further staining.

2. The method of any of claim 1 wherein at least part of the method is performed using an automated tissue processor.

3. The method of any of claim 1 wherein the chemical tissue penetrant enhancer is selected from the group consisting of an aprotic solvent, a surfactant, a non-ionic detergent, an ether, a nitrile, and combinations thereof.

4. The method of any of claim 1 wherein the chemical tissue penetrant enhancer is selected from the group consisting of polyethylene glycol (PEG), polyoxyethylenesorbitan, polyoxyethylene ether, polyoxyethylene 23 lauryl ether (Brij 35), Triton X-100, Nonidet P-40, lysolecithin, saponin, dimethyl sulfoxide (DMSO), tetrahydrofuran, dioxane, ethyl acetate, butyl acetate, isopropyl acetate, toluene, dichloromethane, dichloroethane, chlorobenzene, acetone, acetonitrile, and combinations thereof.

5. The method of any of claim 1 wherein the tissue thickness is up to about 5 mm.

6. The method of any of claim 1 wherein during dehydration, the tissue is treated with a bluing solution.

7. The method of any of claim 1 wherein the processing is initiated with the tissue held in a buffered formalin/alcohol solution.

8. The method of any of claims 1 wherein the stain is at least one of hematoxylin or eosin-Y.

9. The method of any of claims 1 wherein the tissue sample is fixed using formalin.

10. A method for dehydrating and staining a fixed tissue sample up to 5 mm thick prior to infiltrating with an embedding medium, the method comprising
exposing the tissue sample sequentially to
   a. a hematoxylin stain reagent comprising hematoxylin, an oxidizer, and a mordant;
   b. an aqueous solution comprising about 85% to about 95% reagent grade alcohol at about pH 8.2 to about pH 8.5;
   c. an eosin stain reagent comprising eosin-Y in an acidic alcohol solution comprising about 80% alcohol at about pH 4.5 to about pH 4.8; and
thereafter dehydrating and infiltrating the tissue sample with an embedding medium.

11. The method of claim 10 wherein at least steps a, b, and c are performed using centrifugal pressure.

12. The method of claim 10 wherein at least steps a, b, and c are performed using centrifugal pressure, step a is performed at about 55° C., and step b is performed at about 30° C.

13. The method of claim 10 wherein the hematoxylin stain reagent comprises a compound selected from the group consisting of dimethylsulfoxide, ethylene glycol, polyethylene glycol, a surfactant, and combinations thereof.

14. The method of claim 10 wherein the eosin stain reagent comprises a compound selected from the group consisting of dimethylsulfoxide, a surfactant, and combinations thereof.

\* \* \* \* \*